US005811079A

United States Patent [19]
Yu et al.

[11] Patent Number: 5,811,079
[45] Date of Patent: Sep. 22, 1998

[54] ANTICALCULUS DENTIFRICE COMPOSITION CONTAINING HIGHLY SOLUBLE PYROPHOSPHATE

[75] Inventors: Dahsehn Yu, Randolph; Anil K. Talwar, Long Valley; D. Scott Harper, Glen Rock; Dhananjaya Alli, West Orange, all of N.J.

[73] Assignee: Warner-Lambert Company, Morris Plains, N.J.

[21] Appl. No.: 795,921

[22] Filed: Feb. 5, 1997

Related U.S. Application Data

[60] Provisional application No. 60/011,345, Feb. 8, 1996.

[51] Int. Cl.$^6$ .............................. A61K 7/16; A61K 7/18; A61K 7/26
[52] U.S. Cl. .............................. 424/52; 424/49; 424/57; 424/58
[58] Field of Search .......................................... 424/49–58

[56] References Cited

U.S. PATENT DOCUMENTS

| | | |
|---|---|---|
| 3,927,202 | 12/1975 | Harvey et al. . |
| 3,959,458 | 5/1976 | Agricola et al. . |
| 4,193,973 | 3/1980 | Jarvis et al. . |
| 4,247,526 | 1/1981 | Jarvis et al. . |
| 4,323,551 | 4/1982 | Parran, Jr. . |
| 4,545,979 | 10/1985 | Ambike et al. . |
| 4,550,018 | 10/1985 | Ambike et al. . |
| 4,806,342 | 2/1989 | Gaffar et al. . |
| 4,822,599 | 4/1989 | Mitra . |
| 4,869,898 | 9/1989 | Gaffar et al. . |
| 4,889,712 | 12/1989 | Gaffar et al. . |
| 4,913,895 | 4/1990 | Miyake et al. . |
| 4,921,693 | 5/1990 | Gaffar et al. . |
| 4,925,655 | 5/1990 | Smigel et al. . |
| 4,945,087 | 7/1990 | Talwar et al. . |
| 4,985,236 | 1/1991 | Ibrahim et al. . |
| 4,992,276 | 2/1991 | Dills et al. . |
| 4,996,042 | 2/1991 | Wagner . |
| 5,011,830 | 4/1991 | Leonard et al. . |
| 5,015,464 | 5/1991 | Strobeidge . |
| 5,015,467 | 5/1991 | Smitherman . |
| 5,017,362 | 5/1991 | Gaffar et al. . |
| 5,094,844 | 3/1992 | Gaffar et al. . |
| 5,143,719 | 9/1992 | Elliott et al. . |
| 5,145,666 | 9/1992 | Lukacovic et al. . |
| 5,145,667 | 9/1992 | Ibrahim et al. . |
| 5,176,901 | 1/1993 | Gallopo et al. . |
| 5,180,576 | 1/1993 | Winston et al. . |
| 5,215,740 | 6/1993 | Domke et al. . |
| 5,240,697 | 8/1993 | Norfleet et al. . |
| 5,256,402 | 10/1993 | Prencipe et al. . |
| 5,292,526 | 3/1994 | Gaffar et al. . |
| 5,294,432 | 3/1994 | Winston et al. . |
| 5,298,238 | 3/1994 | Husselin et al. . |
| 5,318,773 | 6/1994 | Winston et al. . |
| 5,334,375 | 8/1994 | Nabi et al. ................................. 424/52 |
| 5,352,439 | 10/1994 | Norfleet et al. . |
| 5,356,615 | 10/1994 | Gaffar . |
| 5,405,603 | 4/1995 | Mackles et al. . |
| 5,407,662 | 4/1995 | Mackles et al. . |
| 5,472,684 | 12/1995 | Nabi et al. . |
| 5,472,685 | 12/1995 | Gaffar . |
| 5,578,295 | 11/1996 | Francis et al. . |
| 5,628,986 | 5/1997 | Sanker et al. . |
| 5,723,500 | 3/1998 | Stringer et al. ......................... 514/736 |

FOREIGN PATENT DOCUMENTS

| | | |
|---|---|---|
| 249398 | 12/1987 | European Pat. Off. . |
| 331415 | 6/1989 | European Pat. Off. . |
| 345821 | 12/1989 | European Pat. Off. . |
| 483111 | 4/1992 | European Pat. Off. . |
| 469722 | 5/1992 | European Pat. Off. . |
| 88-3817014 | 5/1988 | Germany . |
| 3942644 | 2/1991 | Germany . |

(List continued on next page.)

OTHER PUBLICATIONS

Frenius' Z. Anal. Chem. (1972), 260(1) pp. 25–29 Hans Koenig, et al. (Abstract Only).
Abstracts of Non: Patent Documents.
Product Alert Jul. 11, 1994 "Listerine Toothpaste—Coolmint".
Cosmetics International Apr. 25, 1995: 7 "Listerine Toothpaste Due".
Lookout (Non–Foods Edition) Sep. 12, 1995 "Listerine Coolmint Toothpaste".
Product Alert Sep. 11, 1995 "Listerine Toothpaste—Coolmint Gel; Paste".
New Product News 33(8):54 Sep. 14, 1997 "Cool Mint Listerine Tarter Control Toothpaste".
New Product news 33(4):52 May 12, 1997 "Cool Mint Listerine Tarter Control Gel Toothpaste".
New Product News 32(4):49–50 May 8, 1996 "Cool Mint Listerine Gel Toothpaste".
New Product News 31(8):46 Sep. 13, 1995 "Listerine Toothpaste".
New Product News 31(6): 42 Jul. 12, 1995 "Listerine Toothpaste".
Weisz, D. Brandweek 36(22): 4 May 29, 1995 "Listerine Paste Intro to Ambush Total".
Weisz, D. Brandweek 36(16): 6 Apr. 17, 1995 "Listerine Toothpaste Set for Fall".
Drug Store News Nov. 4, 1996: 4 "Listerine Toothpaste by Warner Lambert".
OTC Update Sep. 1, 1996 Oral Care Products: Listerine Extends to Toothpaste.

*Primary Examiner*—Shep K. Rose
*Attorney, Agent, or Firm*—Jean B. Barish; Evan J. Federman

[57] ABSTRACT

An anticalculus dentifrice composition containing an antimicrobially effective amount of an antimicrobial agent selected from the group consisting of thymol, eucalyptol, methyl salicylate and mixtures thereof, and a pyrophosphate ion in an amount from about 0.1% to less than about 1.5% by weight of the composition, the pyrophosphate ion being derived from a highly soluble alkali metal pyrophosphate salt. The composition exhibits both antimicrobial and anticalculus efficacy at low levels of pyrophosphate ion even in the substantial absence of anticalculus enhancing agents.

20 Claims, No Drawings

FOREIGN PATENT DOCUMENTS

| | | |
|---|---|---|
| 4305278 | 7/1993 | Germany . |
| 4418796 | 12/1994 | Germany . |
| 49-133535 | 12/1974 | Japan . |
| 5551013 | 4/1980 | Japan . |
| 2032010 | 1/1990 | Japan . |
| 0259512 | 2/1991 | Japan . |
| 3200712 | 9/1991 | Japan . |
| 2200551 | 8/1988 | United Kingdom . |
| 2201593 | 9/1988 | United Kingdom . |
| 2235133 | 2/1991 | United Kingdom . |
| 9517879 | 7/1995 | WIPO . |
| 96/03109 | 2/1996 | WIPO . |

ANTICALCULUS DENTIFRICE COMPOSITION CONTAINING HIGHLY SOLUBLE PYROPHOSPHATE

BACKGROUND OF THE INVENTION

REFERENCE TO RELATED APPLICATIONS

This application was filed as Provisional Application Ser. No. 60/011,345 on Feb. 8, 1996.

FIELD OF THE INVENTION

This invention relates to anticalculus dentifrices, such as toothpastes, gels and tooth powders, containing highly soluble pyrophosphate salts and an antimicrobially effective amount of an antimicrobial agent selected from the group consisting of thymol, eucalyptol, methyl salicylate and mixtures thereof. Optionally, one or more other essential oils, such as menthol or anethole, may also be included.

RELATED BACKGROUND ART

Dental calculus, also known as tartar, is the solid hard mass of calcified material that forms on the surfaces of the teeth. Mature calculus consists of an inorganic portion, which is mostly calcium phosphate arranged in a hydroxyapatite (HAP) crystal lattice, and an organic portion consisting of desquamated epithelial cells, leukocytes, salivary sediment, food debris and various microorganisms. Over time, the mature calculus develops a visible color which is aesthetically undesirable. Periodic dental visits to remove calculus by mechanical means is quite common.

Many compositions have been developed in an attempt to inhibit calculus formation or to remove calculus after it has formed. It is well known that pyrophosphate salts can be employed to inhibit or retard formation of calculus. For example, U.S. Pat. No. 4,323,551 generically describes a mouthwash composition containing about 0.02% to 0.20% of a quaternary ammonium compound, such as cetylpyridium chloride, and an amount of tetra-alkali metal pyrophosphate salt sufficient to provide about 0.5% to 5% of the $P_2O_7^{-4}$ ion. Dentifrices, such as toothpaste, or the use of antimicrobially effective amounts of an essential oil in a dentifrice are not disclosed or suggested.

Generally it has been believed that pyrophosphates must be protected from significant hydrolysis in the oral cavity to remain effective inhibitors of calculus at a relatively low concentration. U.S. Pat. No. 4,889,712 is directed to an oral composition containing from about 0.1 to 7% of a water soluble linear molecularly dehydrated alkali metal or ammonium polyphosphate and a synthetic anionic polymeric polycarboxylate salt in a particular ratio. The polycarboxylate salt is employed to reduce the amount of pyrophosphate in attempt to overcome the problems associated with grittiness of relatively insoluble tetrasodium pyrophosphate or the bitter taste of the more soluble tetrapotassium pyrophosphate.

Similarly, U.S. Pat. No. 5,180,576 is directed to reducing the amount of pyrophosphate needed in an anticalculus dentifrice by the inclusion of sodium bicarbonate. The bicarbonate is said to enhance the calculus inhibiting properties of the pyrophosphate salts so that lesser amounts, e.g. less than 1.5% $P_2O_7^{-4}$ ions, of the pyrophosphate salts are needed.

The belief that an anticalculus enhancing agent is required when relatively low levels of pyrophosphate are employed is further described in Schiff, T. G., et al., "The Comparative Anticalculus Effect of Dentifrices Containing 1.30% Soluble Pyrophosphate With and Without a Copolymer," The Journal of Clinical Dentistry, Vol. II, No. 2, 48–52 (1990). This publication discloses that a dentifrice containing 1.30% soluble pyrophosphate (from 2.0% tetrasodium pyrophosphate) and 1.50% of a copolymer of methoxyethylene and maleic acid significantly reduced calculus formation while a similar dentifrice without the copolymer did not. Only relatively insoluble tetrasodium pyrophosphate was used. None of the above described prior art discloses or suggests the use of antimicrobially effective amounts of essential oils in a dentifrice.

Volatile or essential oils are widely used in oral care products. Essential oils are aromatic compounds that are either derived from plant sources or are synthesized. Some essential oils show long-lasting germicidal effectiveness against the most common pathogens in the mouth. These pathogens are frequently associated with oral malodor, plaque, and gingivitis. Thymol is an essential oil that is well-known and widely used as an antimicrobial in oral care products. Other essential oils include menthol, methyl salicylate, eucalyptol, anethole and eugenol.

Essential oils have been used for years in antiseptic and antiplaque mouthwash solutions. For example, LISTERINE® antiseptic mouthwash has been marketed since 1881, and contains the essential oils thymol, menthol, eucalyptol, and methyl salicylate. More recently, essential oils have been included in formulations of toothpaste. U.S. Pat. No. 1,526,940 describes a toothpaste with the germicide ammonium ichthyol sulphonate with high amounts of thymol, menthol, eucalyptol, methyl salicylate, and peppermint oil as flavorants and taste-masking ingredients.

U.S. Pat. No. 3,164,524 is directed to an oral antiseptic comprising 2,2'-thiobis-(4,6-dichlorophenol), boric acid, methyl salicylate, thymol, menthol and eucalyptol.

U.S. Pat. No. 5,094,843 to describes an anti-plaque, anti-gingivitis toothpaste with a fluorine source, and a specific range of thymol, menthol, methyl salicylate and eucalyptol.

A dentifrice composition with essential oils having enhanced antiseptic activity at a pH between about 3.0 and about 5.5 is disclosed in copending application No. 08/280,098, entitled "Antiseptic Dentifrice", filed Jul. 25, 1994, the disclosure of which is incorporated by reference herein. This application corresponds to WO 96/03109. The dentifrice contains 0.01% w/w to about 1.0% w/w thymol, 0.01% w/w to about 1/0% w/w eucalyptol, 0.01% w/w to about 1.0% w/w methyl salicylate, 0.015% w/w to about 1.0% w/w menthol and 0.1% to about 1.0% w/w of a fluoride releasing compound so as to release 800 to 1500 ppm F. The reduction or inhibition of calculus with pyrophosphates, however, is not described.

PCT International Publication No. WO 95/17879 generically describes an oral composition having about 3200 ppm to about 4500 ppm of thymol, from about 1.5% to about 10% of one or more water soluble alkali metal pyrophosphate ion source, and from about 89% to about 28% of one or more carrier materials. This publication indicates that the amount of tetrasodium pyrophosphate that may be useful is enough to provide at least 1.0% $P_2O_7^{-4}$, and preferably from about 1.5% to about 10% by weight of the composition. Anticalculus enhancing agents, such as synthetic anionic polymers, are said to be optional. This publication also exemplifies the use of 6.832% tetrapotassium pyrophosphate (60%) in a dentifrice composition. However, there is no disclosure or suggestion of a composition having a low-level of pyrophosphate ion derived from a highly soluble alkali metal pyrophosphate.

U.S. Pat. No. 4,913,895 is directed to a method of applying an oral composition containing at least one phosphate selected from certain linear polyphosphates or cyclic polyphosphates and menthol, anethole or mixtures thereof. The composition is said to provide antibacterial efficacy and prevent the development of calculus and periodontal disease. This patent discloses a toothpaste composition containing 1-menthol and 1.37% $P_2O_7^{-4}$ ions derived from tetrapotassium pyrophosphate. However, there is no recognition of the benefit of employing highly soluble alkali metal pyrophosphates in combination with thymol.

SUMMARY OF THE INVENTION

This invention relates to an anticalculus dentifrice composition comprising: (a) an antimicrobially effective amount of an antimicrobial agent selected from the group consisting of thymol, eucalyptol, methyl salicylate and mixtures thereof; (b) a pyrophosphate ion in an amount from about 0.1% to less than about 1.5% by weight of the composition, wherein said pyrophosphate ion is derived from a highly soluble alkali metal pyrophosphate salt; and (c) an orally acceptable carrier. Preferably the antimicrobial agent includes thymol and most preferably is a combination of at least thymol, eucalyptol, methyl salicylate and menthol. Significantly, the anticalculus composition of this invention is substantially free of known anticalculus enhancing agents employed to inhibit the hydrolysis of pyrophosphate in the oral cavity.

The highly soluble alkali metal pyrophosphate employed in this invention typically has an aqueous solubility greater than 200 g/kg, and preferably greater than 500 g/kg at 25° C. Tetrapotassium pyrophosphate is highly preferred.

The anticalculus dentifrice of this invention provides antimicrobial efficacy to inhibit plaque in combination with anticalculus efficacy using an advantageously low level of highly soluble alkali metal pyrophosphate.

Another embodiment of this invention relates to a method for inhibiting the formation of calculus on the surfaces of teeth, comprising the step of applying the above-described anticalculus dentifrice composition to the teeth. Generally the step of applying is performed through the use of a tooth brush, although other application means may also be employed.

DETAILED DESCRIPTION OF THE INVENTION

Dentifrice compositions of this invention contain both an antimicrobially effective amount of thymol and optionally one or more other essential oils and a highly soluble alkali metal pyrophosphate that provides about 0.1% to less than about 1.5% of $P_2O_7^{-4}$ ion in the composition. Preferably, the pH of the dentifrice composition of this invention is adjusted to between about 7 and 10 to enhance the stability of the composition.

Highly soluble alkali metal pyrophosphates generally have an aqueous solubility of at least 200 g/kg, more preferably at least 500 g/kg and most preferably greater than 1000 g/kg at 25° C. Pyrophosphates are well known to those of ordinary skill in the art. A particularly preferred highly soluble alkali metal pyrophosphate is tetrapotassium pyrophosphate having an aqueous solubility of 1870 g/kg at 25° C.

Significantly, the dentifrice compositions of this invention are substantially free of anticalculus enhancing agents. Such anticalculus enhancing agents include synthetic anionic polymeric polycarboxylates (disclosed, for example, in U.S. Pat. Nos. 4,806,342, 4,869,898, 4,889,712, 4,921,693, 5,043,154, and U.S. Pat. No. 5,017,362), polyvinlyphosphate (disclosed in U.S. Pat. No. 5,094,844), sodium bicarbonate (disclosed in U.S. Pat. No. 5,180,526), phosphono-containing cotelomers of acrylic acid/maleic acid (disclosed in U.S. Pat. No. 5,143,719) and the like. For the purposes of this invention, anticalculus enhancing agents include compounds which when provided in an effective amount will inhibit the hydrolysis of pyrophosphates in the oral cavity.

Essential oils are volatile aromatic oils which may be synthetic or may be derived from plants by distillation, expression or extraction, and which usually carry the odor or flavor of the plant from which they are obtained. In the dentifrice composition of this invention, antiseptic activity is provided by essential oils. Some of these essential oils also act as flavoring agents. Besides thymol, the essential oils of this invention may include but are not limited to menthol, methyl salicylate (wintergreen oil), eucalyptol, carvacrol, camphor, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, peppermint oil, lemon oil, orange oil, sage oil, rosemary oil, cinnamon oil, pimento oil, laurel oil, cedar leaf oil, and clove oil. Essential oils may be in the dentifrice composition of the present invention in an amount of from about 0.01% w/w to about 5.0% w/w; preferably in an amount of from about 0.05% w/w to about 4.0% w/w; and more preferably in an amount of from about 0.1% w/w to about 3.0% w/w. A particularly preferred combination of essential oils includes thymol, menthol, eucalyptol and methyl salicylate.

Thymol, also known by the chemical formula 5-methyl-2-(1-methylethyl) phenol, is obtained from the essential oil of *Thymus vulgaris Labiatae* and *Monarda punctata Labiatae*. Thymol is a white crystalline powder with an aromatic odor and taste and is soluble in organic solvents but only slightly soluble in deionized water. Thymol is included in the dentifrice composition of this invention in an amount of from about 0.01% w/w to about 1.5% w/w; preferably in an amount of from about 0.025% w/w to about 1.0% w/w; and most preferably in an amount of from about 0.05% w/w to about 0.8% w/w.

Menthol is isolated principally from the oil of *Mentha arvensis*. In its commercial form, menthol is available as L-menthol crystals obtained from a process involving cooling of the oil. Fractional distillation of peppermint oil which usually contains from about 40% to about 65% menthol represent another important source of menthol. Synthetic sources of L-menthol are also available. Menthol may be in the dentifrice composition of the present invention in an amount of from about 0.01% w/w to about 3.0% w/w; preferably in an amount of from about 0.05% w/w to about 2.5% w/w; and most preferably in an amount of from about 0.1% w/w to about 2.0% w/w.

Eucalyptol, another essential oil with antiseptic properties, is derived from the eucalyptus tree. Having a camphoraceous odor and cooling taste, this essential oil is often combined with other essential oils such as menthol in confection formulations to impart medicinal effect. Combinations of menthol and eucalyptol are widely used. Particularly preferred uses of the menthol-eucalyptol combination include, according to the present invention, dentifrices such as toothpastes or dental gels. Eucalyptol may be in the dentifrice composition of the present invention in an amount of from about 0.01% w/w to about 1.5% w/w; preferably in an amount of from 0.025% w/w to about 1.0% w/w; and most preferably in an amount of from about 0.05% w/w to about 0.8% w/w.

Methyl salicylate is the main ingredient in many essential oils, constituting about 99% of oil of wintergreen (*Gaultheria procumbens*) and sweet birch (*Betula lenta*). Methyl salicylate, which has a distinctive refreshing aroma, is used widely in mouthwashes, chewing gums and other oral and pharmaceutical preparations. Methyl salicylate may be in the dentifrice composition of the present invention in an amount of from about 0.01% w/w to about 3.0% w/w; preferably in an amount of from about 0.05% w/w to about 2.5%; and most preferably in an amount of from about 0.1% w/w to about 2.0% w/w.

The dentifrice composition of the invention may contain the following essential oils in percentages by weight: (a) thymol from about 0.01% w/w to about 1.5% w/w; (b) menthol from about 0.01% w/w to about 3.0% w/w; (c) eucalyptol from about 0.01% w/w to about 1.5% w/w; and (d) methyl salicylate from about 0.01% w/w to about 3.0% w/w.

In the preferred embodiment of the dentifrice composition of the present invention, the dentifrice composition may contain the following essential oils in percentages by weight: (a) thymol from about 0.025% w/w to about 1.0% w/w; (b) menthol from about 0.05% w/w to about 2.5% w/w; (c) eucalyptol from about 0.025% w/w to about 1.0% w/w; and (d) methyl salicylate from about 0.05% w/w to about 2.5% w/w.

In the most preferred embodiment of the dentifrice composition of the present invention, the dentifrice composition may contain the following essential oils in percentages by weight: (a) thymol from about 0.05% w/w to about 0.8% w/w; (b) menthol from about 0.1% w/w to about 2.0% w/w; (c) eucalyptol from about 0.05% w/w to about 0.8% w/w; and (d) methyl salicylate from about 0.1% to about 2.0% w/w.

Fluoride-releasing compounds may be used in this invention and may be fully or slightly water soluble, and are characterized by their ability to release fluoride ions or fluoride-containing ions in water and by their lack of reaction with other components in the composition. In the dentifrice composition of this present invention, anticaries activity is provided by fluoride-releasing compounds. Typical fluoride-releasing compounds are inorganic fluoride salts such as water-soluble alkaline earth metal, alkali metal, and heavy metal salts. Sodium monofluorophosphate, sodium fluoride, stannous fluoride and mixtures thereof are preferred.

The amount of fluoride-releasing compound present in a preferred embodiment of this invention depends upon the type of fluoride-releasing compound employed, the solubility of the fluoride-releasing compound, and the formulation of the dentifrice composition. The fluoride-releasing compound used must be used in a nontoxic amount. In general, the fluoride-releasing compound, when used, will be present in an amount by weight of up to about 1.2% w/w, preferably from about 0.1% w/w to about 1.0% w/w, and most preferably from about 0.175% w/w to about 0.8% w/w, of the dentifrice composition so as to release about 800 to 1500 ppm $F^-$.

The most preferred fluoride-releasing compound in the dentifrice composition of the invention is sodium fluoride at a concentration from about 0.1% w/w to about 1.0% w/w, more preferably about 0.15% w/w to about 0.8% w/w, or most preferably, 0.24% w/w.

The pH for the preferred embodiment according to the present invention is from about 7 to about 10, more preferably from about 7.5 to about 9. A pH within these ranges has been found to enhance the storage stability of the dentifrice composition.

The preferred embodiment of the present invention may also contain conventional dentifrice additives including but not limited to humectants, binders, thickeners, surfactants, preservatives, sweeteners, flavors, colors, and a buffer. These additives are present in amounts that do not interfere with the antiseptic and anticaries properties of the composition of the present invention.

Surfactants or surface active agents are organic compounds which reduce surface tension between liquids and aid in the dispersion of a composition throughout the oral cavity. The surfactant in the present invention may be anionic, nonionic, or amphoteric. The oral hygiene or dentifrice compositions of the present invention may contain surfactants in amounts up to about 5.0% w/w; preferably from about 0.1% w/w to about 3.0% w/w of the dentifrice composition; and most preferably from about 0.2% w/w to about 2.5% w/w of the dentifrice composition.

The most preferred surfactants are anionic. These anionic surfactants include but are not limited to sodium lauryl sulfate, sodium lauroyl sarcosinate, sodium methyl cocyl taurate, and disodium lauryl sulfosuccinate.

In the most preferred embodiment the surfactant is the anionic surfactant sodium lauryl sulfate.

Amphoteric surfactants having the capacity to behave as either an acid or a base and include quaternized imidazole derivatives useful in the present invention. Preferred amphoteric surfactants include long chain (alkyl) amino-alkylene aklyated amine derivatives, also known as MIRANOL®, manufactured by Rhone-Poulanc, Cranberry, N.J.

Sweeteners well known in the art, including natural and artificial sweeteners, may be used. The sweetener may be selected from a wide range of materials including naturally occurring water-soluble sweeteners, artificial water-soluble sweeteners and modified water-soluble sweeteners derived from naturally occurring water-soluble sweeteners. Artificial water-soluble sweeteners include, but are not limited to, soluble saccharin salts, e.g., sodium or calcium saccharin salts, cyclamate salts, the sodium, ammonium or calcium salt of 3,4-dihydro-6-methyl-1,2,3,-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like; dipeptide based sweeteners, such as L-aspartic acid derived sweeteners, e.g., L-aspartyl-L-phenylalanine methyl ester (Aspartame) and materials described in U.S. Pat. No. 3,492,131, L-alpha-aspartyl-N-(2,2,4,4-tetramethyl-3-thietanyl)-3-alaninamide hydrate (Alitame), methyl esters of L-aspartyl-L-phenylglycerine, and L-aspartyl-L-2,5-dihydrophenylglycine, L-aspartyl-2,5-dihydro-L-phenylalanine; L-aspartyl-L-(1-cyclohexene)-alanine, and the like. Naturally occurring water-soluble sweeteners include, but are not limited to, sugar alcohols, including sorbitol as 70% sorbitol solution, mannitol, xylitol, maltitol, hydrogenated starch hydrolysates and mixtures thereof.

Water-soluble sweeteners derived from naturally occurring water-soluble sweeteners include, but are not limited to, chlorinated derivatives of sucrose, known, for example, under the product designation of Sucralose; and protein-based sweeteners such as thaumaoccous danielli (Thaumatin I and II).

Sorbitol solution supplies sweetness and body to the composition and gives a desirable mouth feel. Sorbitol solution also enhances flavor, prevents harsh taste and provides a fresh and lively sensation in the mouth. It also prevents caking of the dentifrice.

In general, an effective amount of sweetener is utilized to provide the level of sweetness desired in any particular embodiment of the dentifrice compositions according to the present invention. This amount will vary with the sweetener selected and the final oral hygiene product. The amount of sweetener normally present is from about 0.0025% w/w to about 60% w/w of the dentifrice composition. The exact range of amounts for each type of sweetener in a dentifrice is well known in the art and is not the subject of the present invention.

The flavors which may be used in the invention include natural and artificial flavors known in the dentifrice art. Suitable flavors include, but are not limited to, mints, such as peppermint, citrus flavors such as orange and lemon, artificial vanilla, cinnamon, various fruit flavors, and the like. Anethole (or anise camphor, p-propenyl anisole) is a flavor constituent of anise and fennel oils which are used widely as flavoring agent and antiseptic, and has been found useful in masking the harsh taste of thymol.

The amount of flavor is normally a matter of preference subject to such factors as the type of final dentifrice composition, the individual flavor employed, and the strength of flavor desired. The flavors are preferably utilized in amounts that may range in total amounts from about 0.01% w/w to about 6% w/w of the dentifrice composition.

Coloring agents in this invention are used in amounts effective to produce a dentifrice of the desired color. These coloring agents may be incorporated in amounts up to about 3% by weight of the dentifrice composition of the present invention. The coloring agents may also include natural food colors and dyes suitable for food, drug and cosmetic applications. These coloring agents are known as FD & C dyes and lakes. The materials acceptable for the foregoing uses are preferably water-soluble. Illustrative nonlimiting examples include the indigoid dye known as FD & C Blue No. 1, and D & C Yellow No. 10. A full recitation of all FD & C colorants and their corresponding chemical structures may be found in the Kirk-Othmer Encyclopedia of Chemical Technology, 3rd Edition, in volume 5 at pages 857–884. A preferred opacifier, titanium dioxide, may be incorporated in amounts up to about 3.0% w/w, preferably less than about 2.0% w/w of the composition, and most preferably less than about 1.0% w/w.

Suitable humectants in this invention include sorbitol, as 70% sorbitol solution, glycerin, propylene glycol, polyethylene glycol, mixtures thereof, and the like. Humectants may be present in amounts from about 1.0% to about 75.0% by weight of the dentifrice composition.

Suitable abrasive substances for use in this invention include hydrated silica, calcium carbonate, calcium pyrophosphate, dicalcium phosphate dihydrate, or alkali metal metaphosphates. Silica abrasives in the dentifrice composition according to this invention may include among others, ZEODENT® (113), manufactured by J. M. Huber Corp. and SYLOID® or SYLODENT®, manufactured by W. R. Grace Co. These polishing agents may be used in amounts up to about 75.0% w/w of the composition, preferably in amounts from about 5.0% w/w to about 50% w/w of the composition, and most preferably from about 5.0% w/w to about 40.0% w/w of the composition.

In the preferred embodiment of this invention, the dentifrice composition includes an oral vehicle and is in the form of toothpaste or a dental gel.

The dentifrice composition of this invention may also include binders or gelling agents to give the products their characteristic consistency. Gelling agents such as hydroxyethyl cellulose, carboxymethyl cellulose, methyl cellulose, xanthan gum, gelling silicas, and the like may be used singly or in combination. The preferred gelling system is a mixture of carboxy methyl cellulose, xanthan gum and gelling silica. Gelling agents may be used in amounts from about 0.1% w/w to about 30% w/w, preferably from about 0.2% w/w to about 15.0% w/w of the dentifrice composition, and most preferably from about 0.4% w/w to about 10% w/w of the composition.

The dentifrice composition of this invention may also contain a desensitizing agent such as strontium chloride, potassium nitrate or sodium citrate, which may be used in an amount from about 0.5% w/w to about 10% w/w.

Suitable preservatives in this invention include sodium Benzoate, butylated hydroxyanisole (BHA), butylated hydroxytoluene (BHT), sodium ascorbate, methyl paraben, propyl paraben, tocopherols and mixtures thereof. Preservatives when used are generally present in amounts up to about 1.0% w/w, and preferably from about 0.01% w/w to about 0.5% w/w of the dental gel composition.

The dentifrice compositions of this invention may be prepared by mixing the desired ingredients using methods well known to those of ordinary skill in the art. For a paste, generally, the pyrophosphate, and any fluoride-releasing compound, and sweetener are mixed with water, followed by the addition of any abrasives and thickeners to form a paste. The essential oils and flavors are preferably mixed and then added to the paste. The preparation of a dental gel employing the ingredients of this invention is also readily accomplished by those having ordinary skill in the art.

This invention also relates to a method for inhibiting the formation of calculus on the surfaces of teeth. The method comprises the step of applying the anticalculus dentifrice composition of this invention to the teeth. Typically a brush is used to apply the composition. Preferably, the method is practiced daily, more preferably twice a day to inhibit the formation of calculus over a period of time. Significantly, low levels of highly soluble alkali metal pyrophosphate, such as tetrapotassium pyrophosphate, are used. Thus, the bitter taste associated with tetrapotassium pyrophosphate is reduced or avoided and compliance with a daily routine of brushing is heightened.

The present invention is further illustrated by the following examples which are, however, not included to limit the effective scope of the claims. All parts and percentages in the examples and throughout the specification and claims are by weight of the final composition (% w/w) unless otherwise specified.

EXAMPLE 1

| Component | % w/w |
|---|---|
| Thymol | 0.40 |
| Methyl Salicylate | 0.17 |
| Menthol | 0.10 |
| Eucalyptol | 0.08 |
| Tetrapotassium Pyrophosphate | 2.47* |
| Sodium Fluoride USP | 0.24 |
| Sodium Saccharin | 1.20 |
| Polyethylene Glycol 1450 NF | 3.00 |
| Sorbitol Solution (70%) | 45.00 |
| Gelling Silica | 8.50 |

-continued

| Component | % w/w |
|---|---|
| Abrasive Silica | 8.00 |
| TiO$_2$ | 0.35 |
| Carboxymethyl Cellulose | 0.90 |
| Glycerin USP | 6.00 |
| Peppermint Oil | 0.30 |
| Flavor 0.46 | |
| Sodium Lauryl Sulfate | 1.5 |
| Deionized Water | 21.33 |

*~1.3% P$_2$O$_7^{-4}$ ion.

Several dentifrice compositions were prepared in a manner similar to Example 1, except that the amount of P$_2$O$_7^{-4}$ ion was varied in a number of the commercially available compositions. These formulations were tested against a regular toothpaste (which contains no pyrophosphates) and a tartar control toothpaste (which contains a mixture of tetrasodium pyrophosphate, tetrapotassium pyrophosphate and disodium pyrophosphate) in rat studies.

The rat studies were conducted by applying each composition to the teeth of individual rats with a cotton swab each morning and afternoon for 5 days a week for a three week period. The calculus formation was scored according to the method of Francis and Briner, Journal of Dental Research, Vol. 48, 1185–1195 (1969). The results are set forth in Table 1.

TABLE I

| Composition | pH | % P$_2$O$_7^{-4}$ | Mean Calculus Score | % Reduction vs. Control |
|---|---|---|---|---|
| A | 7.7 | 3.3% | 34.13 | 48.3% |
| B | 7.7 | 1.3% | 44.57 | 32.5% |
| C | 7.7 | 0.0% | 66.03 | — |
| Tartar Control Toothpaste | 7.6 | 5.0% | 47.57 | 28.0% |
| D | 7.7 | 3.3 | 45.00 | 35.3% |
| E | 7.7 | 1.3% | 49.22 | 29.2% |
| Regular Toothpaste | 6.9 | 0% | 69.57 | — |
| Tartar Control Toothpaste | 7.6 | 5.0% | 38.03 | 45.3% |

The results of the rat calculus studies indicate that the formulation of this invention, i.e. Compositions B and E, were effective at reducing calculus formation even when only 1.3% P$_2$O$_7^{-4}$ ions are present.

EXAMPLE 2 AND COMPARATIVE EXAMPLE 1

Two dentifrice composition were prepared containing the following components:

| | % w/w | |
|---|---|---|
| Components | Ex. 2 | Comp. Ex. 1 |
| Thymol | 0.30 | 0.30 |
| Methyl Salicylate | 0.05 | 0.05 |
| Menthol | 0.16 | 0.16 |
| Eucalyptol | 0.09 | 0.09 |
| Tetrapotassium Pyrophosphate | 2.47* | 6.40** |
| Sodium Fluoride | 0.24 | 0.24 |
| Sodium Saccharin | 0.60 | 0.60 |
| Polyethylene Glycol 1450 NF | 3.00 | 3.00 |
| Sorbitol Solution (70%) | 45.00 | 40.00 |
| Gelling Silica | 8.5 | 8.00 |
| Abrasive Silica | 8.0 | 8.00 |
| TiO$_2$ | 0.35 | 0.35 |
| Carboxymethyl Cellulose | 0.90 | 0.90 |
| Glycerin USP | 6.00 | 6.00 |
| Peppermint Oil | 0.26 | 0.26 |
| Spearmint Oil | 0.09 | 0.09 |
| Flavor 0.50 | 0.50 | |
| Sodium Lauryl Sulfate | 1.50 | 1.50 |
| Phosphoric Acid | — | 0.73 |
| Deionized Water | 21.98 | 22.83 |

*1.3% P$_2$O$_7^{-4}$
**3.3% P$_2$O$_7^{-4}$

The dentifrice composition of Example 2 and Comparative Example 1 were tested for calculus inhibition in a clinical study along with the previously described regular toothpaste and the tartar control toothpaste. The study was divided into two fourteen day phases with a seven day wash-out period between each phase. A dental prophylaxis of teeth #21–28 was conducted prior to performing each phase. On day 14, the facial and lingual surfaces of teeth #22–27 were evaluated for calculus accumulation using the method according to Francis and Briner. During phase 1, all subjects delivered a conventional silica based NaF dentifrice (control) to the lower anterior teeth via a custom-fitted mouthguard, i.e., a tooth shield, and brushed only the teeth that remained exposed twice a day. In the second phase, subjects were separated into four treatment groups on the basis of the phase 1 V-M scores. The subjects then delivered the compositions using the tooth shield in manner described above, with one group continuing to use the control. The results of the clinical tests are set forth in Table II.

TABLE II

| Composition | pH | % P$_2$O$_7^{-4}$ | Mean Calculus Score | % Reduction vs. Control |
|---|---|---|---|---|
| Ex. 2 | 8.1 | 1.3% | 15.47 | 25.4% |
| Comp. Ex. 1 | 7.7 | 3.3% | 16.85 | 18.8% |
| Regular Toothpaste | 6.9 | 0.0% | 20.75 | — |
| Tartar Control Toothpaste | 7.6 | 5.0% | 16.19 | 21.9% |

The clinical results indicate that the dentifrice composition of this invention provides excellent calculus inhibition even with only 1.3% pyrophosphate ion derived from the highly soluble tetrapotassium pyrophosphate.

Other variations and modifications of this invention will be obvious to those skilled in this art. This invention is not limited except as set forth in the following claims.

What is claimed is:

1. An anticalculus dentifrice comprising:
   (a) an antimicrobial agent comprising thymol, eucalyptol, methyl salicylate and menthol,
   (b) a pyrophosphate ion in an anticalculus effective amount from about 0.1% to less than 1.5% by weight of the composition,
   (c) one or more fluoride-releasing compounds,
   (d) a dental abrasive, and
   (e) an orally acceptable vehicle;
wherein the composition is free of an anticalculus enhancing agent, has a pH of about 7.5 to about 10 and the pyrophosphate ion is derived from an alkali metal pyrophosphate salt having an aqueous solubility greater than 200 g/kg at 25° C.

2. The anticalculus dentifrice composition according to claim 1, wherein the antimicrobial agent is present in the composition in an amount from about 0.01% to about 5.0%.

3. The anticalculus dentifrice composition according to claim 1, wherein the highly soluble alkali metal pyrophosphate salt has an aqueous solubility greater than 500 g/kg at 25° C.

4. The anticalculus dentifrice composition according to claim 3, wherein the highly soluble alkali metal pyrophosphate salt is tetrapotassium pyrophosphate.

5. The anticalculus dentifrice composition according to claim 4, wherein about 1.3% by weight of the pyrophosphate ion is present in the composition.

6. The anticalculus dentifrice composition according to claim 5, wherein the antimicrobial agent comprises thymol in an amount from about 0.01% to about 1.5% by weight of the composition; menthol in an amount from about 0.01% to about 3.0% by weight of the composition; eucalyptol in an amount from about 0.01% to about 1.5% by weight of the composition; and methyl salicylate in an amount from about 0.01% to about 3.0% by weight of the composition.

7. The anticalculus dentifrice composition according to claim 1, wherein the fluoride-releasing compound is selected from the group consisting of monofluorophosphate, alkali metal fluoride, stannous fluoride, aluminum monofluorophosphate, aluminum difluorophosphate, and mixtures thereof.

8. The anticalculus dentifrice composition according to claim 7, wherein the fluoride-releasing compound is present in an amount by weight up to about 1.2% by weight of the composition.

9. An anticalculus dentifrice composition comprising:
   (a) an antimicrobially effective amount of a mixture of essential oils comprising: thymol in an amount from about 0.01% to about 1.5% by weight of the composition; menthol in an amount from about 0.01% to about 3.0% by weight of the composition; eucalyptol in an amount from about 0.01% to 1.5% by weight of the composition; and methyl salicylate in an amount from about 0.01% to about 3.0% by weight of the composition:
   (b) an anticalculus effective amount of pyrophosphate ion that comprises about 1.3% w/w of the composition and is derived from tetrapotassium pyrophosphate,
   (c) a fluoride source,
   (d) a dental abrasive, and
   (e) an orally acceptable vehicle;
provided that the composition is free of an anticalculus enhancing agent in an amount effective to inhibit hydrolysis of the tetrapotassium pyrophosphate in an oral cavity and the composition has a pH of about 7.5 to about 10.

10. The anticalculus dentifrice composition according to claim 9, wherein the fluoride source is selected from the group consisting of monofluorophosphate, alkali metal fluoride, stannous fluoride, aluminum monofluorophosphate, aluminum difluorophosphate, and mixtures thereof.

11. The anticalculus dentifrice composition according to claim 10, wherein the fluoride source is present in an amount by weight up to about 1.2% by weight of the composition.

12. The anticalculus dentifrice composition according to claim 9, wherein thymol is in an amount from about 0.025% to about 1.0% by weight of the composition; menthol is in an amount from about 0.05% to about 2.5% by weight of the composition; eucalyptol is in an amount from about 0.025% to 1.0% by weight of the composition; and methyl salicylate is in an amount from about 0.05% to about 2.5% by weight of the composition.

13. The anticalculus dentifrice composition according to claim 12, wherein thymol is in an amount from about 0.05% to about 0.8% by weight of the composition; menthol is in an amount from about 0.1% to about 2.0% by weight of the composition; eucalyptol is in an amount from about 0.05% to 0.8% by weight of the composition; and methyl salicylate is in an amount from about 0.1% to about 2.0% by weight of the composition.

14. A method for inhibiting formation of calculus on surfaces of teeth, comprising the step of applying to the teeth a anticalculus dentifrice composition comprising:
   (a) an antimicrobial agent comprising thymol, eucalyptol, methyl salicylate and menthol,
   (b) a pyrophosphate ion in an anticalculus effective amount from about 0.1% to less than 1.5% by weight of the composition,
   (c) a dental abrasive,
   (d) an orally acceptable vehicle,
   (e) one or more fluoride-releasing compounds; and
wherein the composition is free of an anticalculus enhancing agent, has a pH of about 7.5 to about 10 and the pyrophosphate ion is derived from an alkali metal pyrophosphate salt having an aqueous solubility greater than 200 g/kg at 25° C.

15. The method according to claim 14, wherein the highly soluble alkali metal pyrophosphate salt is tetrapotassium pyrophosphate.

16. The method according to claim 14, wherein the antimicrobial agent is present in the composition in an amount from about 0.01% to about 5.0%.

17. The method according to claim 14, wherein the highly soluble alkali metal pyrophosphate salt has an aqueous solubility greater than 500 g/kg at 25° C.

18. The method according to claim 14, wherein 1.3% by weight of the pyrophosphate ion is present in the composition.

19. The method according to claim 14, wherein the fluoride-releasing compound is selected from the group consisting of monofluorophosphate, alkali metal fluoride, stannous fluoride, aluminum monofluorophosphate, aluminum difluorophosphate, and mixtures thereof.

20. The method according to claim 18, wherein the fluoride-releasing compound is present in an amount by weight up to about 1.2% by weight of the composition.

* * * * *